United States Patent
Rode et al.

(10) Patent No.: US 9,527,826 B2
(45) Date of Patent: Dec. 27, 2016

(54) SINGLE STEP PROCESS FOR CONVERSION OF FURFURAL TO TETRAHYDROFURAN

(71) Applicant: COUNCIL OF SCIENTIFIC & INDUSTRIAL RESEARCH, New Delhi (IN)

(72) Inventors: Chandrasekhar Vasant Rode, Pune (IN); Narayan Shamrao Biradar, Pune (IN); Amol Mahalingappa Hengne, Pune (IN)

(73) Assignee: Council of Scientific & Industrial Research, New Delhi (IN)

(*) Notice: Subject to any disclaimer, the term of this patent is extended or adjusted under 35 U.S.C. 154(b) by 0 days.

(21) Appl. No.: 14/764,881

(22) PCT Filed: Jan. 30, 2014

(86) PCT No.: PCT/IN2014/000072
§ 371 (c)(1),
(2) Date: Jul. 30, 2015

(87) PCT Pub. No.: WO2014/118806
PCT Pub. Date: Aug. 7, 2014

(65) Prior Publication Data
US 2015/0368216 A1    Dec. 24, 2015

(30) Foreign Application Priority Data
Jan. 30, 2013  (IN) ............... 0249/DEL/2013

(51) Int. Cl.
*C07D 307/08*        (2006.01)

(52) U.S. Cl.
CPC ............ *C07D 307/08* (2013.01); *Y02P 20/582* (2015.11)

(58) Field of Classification Search
CPC .................................................. C07D 307/08
See application file for complete search history.

(56) References Cited

U.S. PATENT DOCUMENTS

2010/0099895 A1   4/2010 Wabnitz et al.

OTHER PUBLICATIONS

Surapas Sitthisa, et al. "Hydrodeoxygenation of Fufural Over Supported Metal Catalysts: A Comparative Sutdy of Cu, Pd and Ni"; Catalyst Letters, Kluwer Academic Publishers-Plenum Publishers, NE, Vole. 141, No. 6 (Mar. 29, 2011).

Garcia-Suarez, Eduardo J., "Versatile Dual Hydrogenation-oxidation Nanocatalysts for the Aqueous Transformation of Biomass-derived Platform Molecules"; Green Chemistry, vol. 14, No. 5 (Feb. 29, 2012).

*Primary Examiner* — Golam M M Shameem
(74) *Attorney, Agent, or Firm* — DLA Piper LLP (US)

(57) ABSTRACT

The present patent discloses a one step process for the synthesis of THF and related ring hydrogenated products form furfural using Palladium metal based carbon supported catalyst with high selectivity and 100% conversion in both batch and continuous modes.

10 Claims, 4 Drawing Sheets

SINGLE STEP PROCESS FOR CONVERSION OF FURFURAL TO TETRAHYDROFURAN

CROSS-REFERENCE TO RELATED APPLICATIONS

Figure 1:
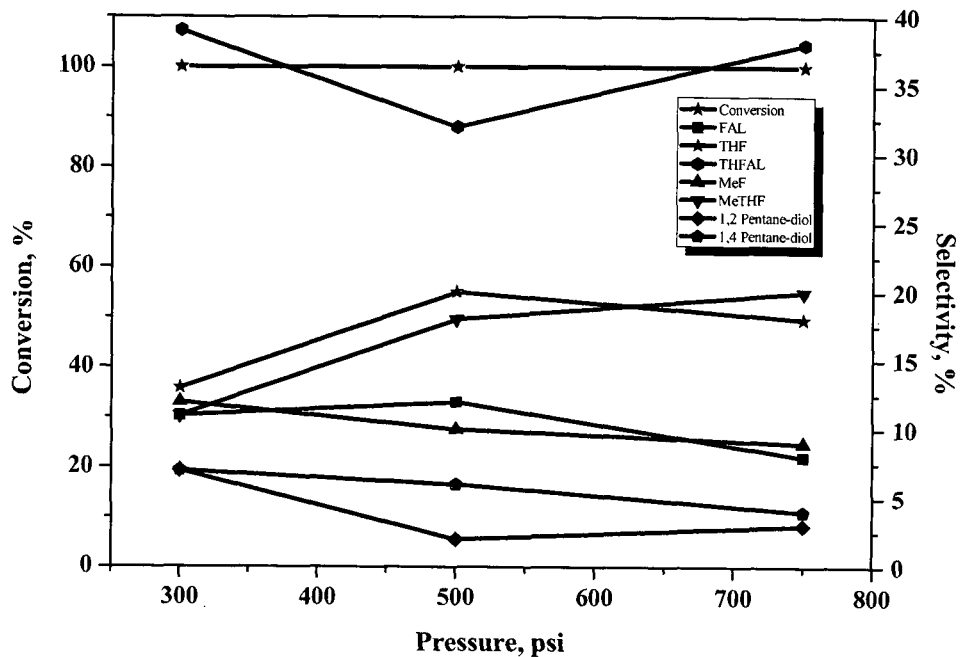

This application is a 35 USC §371 National Stage application of International Application No. PCT/IN2014/000072 filed Jan. 30, 2014, now pending; which claims the benefit under 35 USC §119(a) to India Application Serial No. 0249/DEL/2013 filed Jan. 30, 2013. The disclosure of the prior application is considered part of and is incorporated by reference in the disclosure of this application.

FIELD OF THE INVENTION

The present invention relates to single step process for production of tetrahydrofuran (THF), an industrially useful solvent by hydrogenation of furfural using Pd/C catalyst.

BACKGROUND OF THE INVENTION

Utilization of biomass has received a lot of attention for the development of a sustainable society. Manufacture of organic commodity chemicals from biomass is one of the most important methods of future biomass utilization because biomass is the only renewable source of carbon. Lignocelluloses biomass acts as a more promising feedstock for downstream applications which is more abundant, cheaper and potentially more sustainable.

Furfural is typically used as a precursor in the production of tetrahydrofuran (THF), an important industrial solvent.

Furfural is obtained from the dehydration of pentoses, five carbon sugars, such as xylose and arabinose, commonly obtained by acid-catalyzed digestion of hemicellulose-rich agricultural wastes. The acid hydrolysis of pentose sugars followed by dehydration of three water molecules gives furfural (C5). Furfural (FFR) deserves an attention as a potential platform molecule for production of variety of value added chemicals and fuels such as furan, furfuryl alcohol (FA), tetrahydrofurfuryl alcohol (THFA), 2-methyl furan (2-MF) tetrahydrofuran and 2-methyl tetrahydrofuran (2-MTHF), in which tetrahydrofuran can be produced by decarbonylation of furfural to furan under reductive conditions and then subsequently hydrogenated to tetrahydrofuran (THF). It possesses wide applications; it can be used as solvent, monomer for polymer and chemical.

However depending upon reaction conditions and catalytic properties, hydrogenation of FFR gives variety of products, all of which are important intermediates in the chemical industry.

Conventionally, THF can be produced by number of different routes including dehydration of 1,4-butanediol (BDO) and hydrogenation of maleic anhydride, all these processes contains multi-step synthesis by using reagents and metal complexes for production of THF, out of these one is starting from acetylene and formaldehyde in the presence of a cuprous acetylene complex to form butynediol (Reppe Process), while these processes were dependent on petroleum feedstock.

These processes suffer from a variety of deficiencies such as multi-step synthesis, heavy metal complexes, reagents and harsh reaction conditions which is directly relevant to environmental hazardous.

Hence, these drawbacks may be overcome by either novel catalytic system and/or a single step process for synthesis of THF from furfural which bio-renewable.

There are many supported noble (Pt, Pd, Ru, Rh) and non-noble (Cu, Ni,) metals that have been reported for the hydrogenation of FFR. Mahajani et al in Ind. Eng. Chem. Res., 2003, 42, 3881-3885 reported 5% Pt/C catalyst to study kinetics of FFR hydrogenation to FA, the order he found was 0.85 at 403-448 K temperature and 1.03-2.06 MPa $H_2$ pressure.

Baijun et al in Applied Catalysis A: General, 1998, 171, 117-122 reported Raney nickel catalyst for furfural hydrogenation to furfuryl alcohol with 98% selectivity.

Twin catalyst system for the continuous conversion of furfural to THF through intermediate furan in supercritical Co2 with high selectivity to THF is reported by M. Poliokoff et. al. in Angew. Chem. Int. Ed., 2010, 49, 8856-8859.

Guha J. Catal., 1985, 91, 254-262 reported vapour phase decarbonylation of furfural over Pd—$Al_2O_3$ catalyst, deactivation of catalyst found by cocking Pd—$Al_2O_3$ catalyst. Resasco in Catal Lett, 2011, 141, 784-791 studied the different silica supported metal catalyst for the hydrogenation of furfural, he proposed 1% Pd/$SiO_2$ catalyst give 20% THF with 69% conversion in a continuous fixed bed reactor.

Nagaraja et al. in J. Mol. Catal. A: Chemical, 2007, 278, 29-37 reported Cu based catalyst for coupling route highlighting the combination FFR hydrogenation and dehydrogenation of cyclohexanol in vapour phase conditions. Vapour phase hydrogenation of FFR studied over Ni/SiO2 catalyst to THFAL via furfuryl alcohol in two step strategy having no selectivity found to be THF.

Recently Rafael et al. in Green Chem., 2012, 14, 1434-1439 reported hydrogenation of furfural using carbon-supported Pd NPs with 90% conversion of FFR and 80% selectivity to THF on micro reactor. In "The electrocatalytic hydrogenation of furanic compounds in a continuous electrocatalytic membrane reactor" by Sara K. Green, Jechan Lee, Hyung Ju Kim, Geoffrey A. Tompsett, Won Bae Kim and George W. Huber in Green Chem., 2013, 15, 1869-1879, demonstrate the use of a continuous-flow electrocatalytic membrane reactor for the reduction of aqueous solutions of furfural into furfuryl alcohol (FA), tetrahydrofurfuryl alcohol (THFA), 2-methylfuran (MF) and 2-methyltetrahydrofuran (MTHF). Protons needed for hydrogenation were obtained from the electrolysis of water at the anode of the reactor. Pd was identified as the most active monometallic catalyst of 5 different catalysts tested for the hydrogenation of aqueous furfural with hydrogen gas in a high-throughput reactor. Thus Pd/C was tested as a cathode catalyst for the electrocatalytic hydrogenation of furfural. At a power input of 0.1 W, Pd/C was 4.4 times more active (per active metal site) as a cathode catalyst in the electrocatalytic hydrogenation of furfural than Pt/C. The main products for the electrocatalytic hydrogenation of furfural were FA (54-100% selectivity) and THFA (0-26% selectivity). MF and MTHF were also detected in selectivities of 8%. Varying the reactor temperature between 30° C. and 70° C. had a minimal effect on reaction rate for furfural conversion. Using hydrogen gas at the anode, in place of water electrolysis, produced slightly higher rates of product formation at a lower power input. Sparging hydrogen gas on the cathode had no effect on reaction rate or selectivity, and was used to examine the addition of recycling loops to the continuous electrocatalytic membrane reactor.

A cursory review of prior arts reveal that there is still a scope in the art to provide an effective catalytic system that provides conversion rates with higher selectivity towards tetrahydrofuran.

OBJECTIVES OF THE INVENTION

Main object of the present invention is to provide single step process for the production of tetrahydrofuran (THF), an industrially useful solvent by hydrogenation of furfural (FFR) using Pd/C catalyst.

Another object of the present invention is to provide an effective catalytic system for the conversion of FFR into THF, an industrially useful solvent with higher conversion rates and good selectivity.

SUMMARY OF THE INVENTION

Accordingly, present invention provides a one step process for the synthesis of Tetrahydrofuran (THF) from furfural in both batch and continuous modes comprising: reacting furfural at a concentration in the range of 5 to 20% in the presence of Palladium metal based carbon supported catalyst at a concentration in the range of 5 to 20% at a temperature in the range of 423-513 K in presence of hydrogen at an elevated pressure to obtain THF with 10% to 41% selectivity and related ring hydrogenated products, wherein conversion percentage of furfural is 100%.

In an embodiment of the present invention, the concentration of furfural is 5% by weight.

In another embodiment of the present invention, the selectivity is 20% for batch mode and 41% for continuous mode.

In yet another embodiment of the present invention, the elevated pressure is in the range of 3 to 4 MPa for batch mode and 20 to 50 bar pressure for continuous mode.

In yet another embodiment of the present invention, the elevated pressure is in the range of 30-35 bar pressure for continuous mode.

In yet another embodiment of the present invention, the yield of THF is in the range of 20% for batch mode and 40% for continuous mode.

In yet another embodiment of the present invention, the temperature is 493 K for batch mode and in the range of 423 to 513 K for continuous mode.

In yet another embodiment of the present invention, the temperature is in the range of 473 to 493 K for continuous mode.

In yet another embodiment of the present invention, the related ring hydrogenated products are selected from the group consisting of methyl tetrahydrofuran (MTHF), tetrahydrofurfuryl alcohol (THFAL), Methyl Furan, and Pentanediol.

In yet another embodiment of the present invention, said catalyst is recyclable.

BRIEF DESCRIPTION OF ACCOMPANYING DRAWINGS

FIG. 1 depicts the effect of hydrogen at an elevated pressure under reaction conditions: Furfural, 5% (W/W); Solvent, Isopropyl alcohol (95 ml); Temperature, 493K; Agitation Speed, 1000 rpm; Catalyst, (3% Pd/C), 0.5 gm; Reaction time 5 h.

Figure 2:
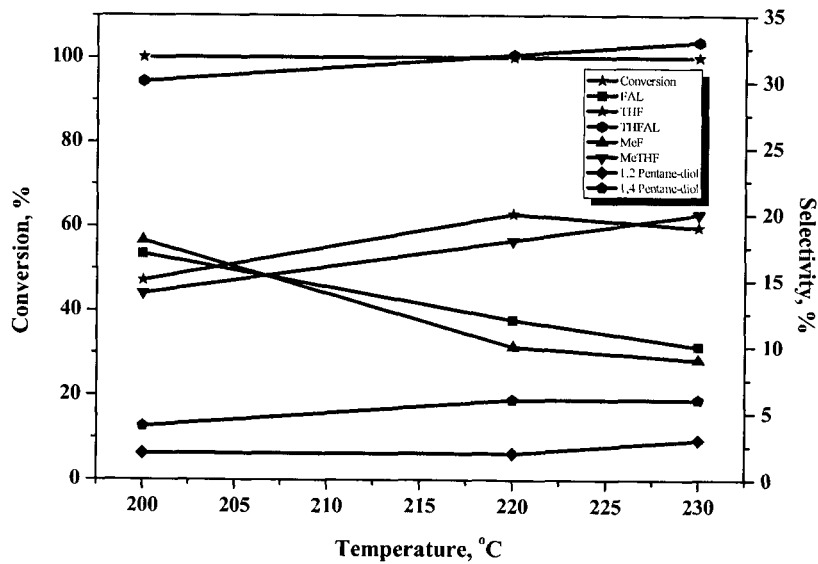

FIG. 2 shows the effect of temperature under reaction conditions: Furfural, 5% (W/W); Solvent, Isopropyl alcohol (95 ml); Pressure, 500 psi; Agitation Speed, 1000 rpm; Catalyst, (3% Pd/C), 0.5 gm; Reaction time 5 h.

Figure 3:
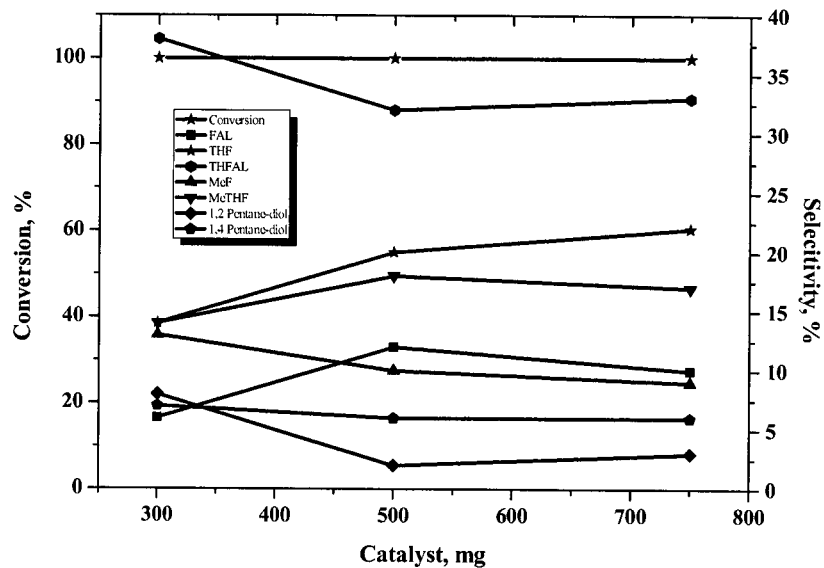

FIG. 3 depicts the effect of catalyst loading under reaction conditions: Solvent, Isopropyl alcohol (95 ml); Temperature 493 K; Pressure, 500 psi; Agitation Speed, 1000 rpm; Catalyst, (3% Pd/C), 0.5 gm; Reaction time 5 h.

Figure 4:
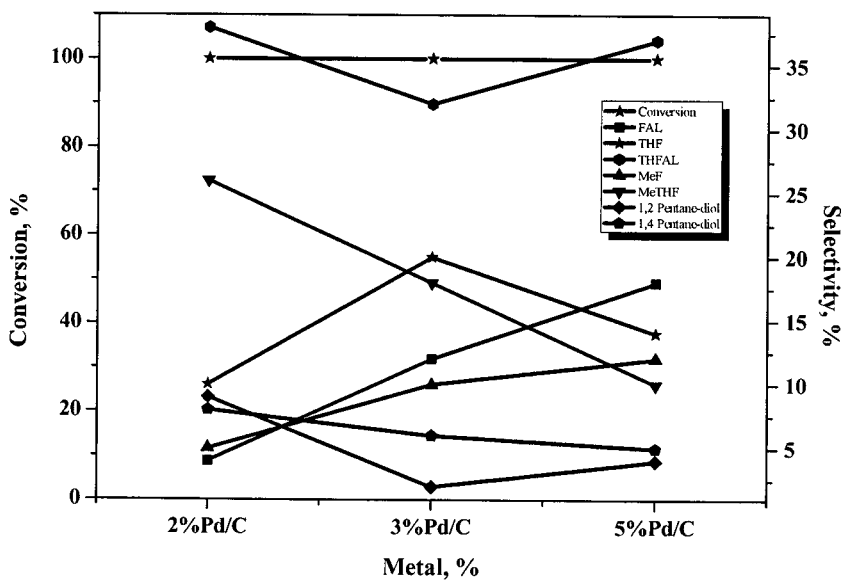

FIG. 4 shows the effect of metal loading under reaction conditions: Furfural, 5% (W/W); Solvent, Isopropyl alcohol (95 ml); Temperature 493 K; Pressure, 500 psi; Agitation Speed, 1000 rpm; Catalyst, (Pd/C), 0.5 gm; Reaction time 5 h.

Figure 5:
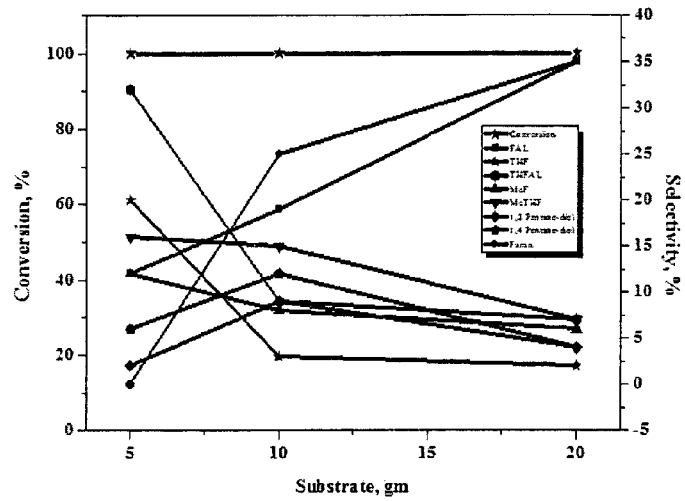

FIG. 5 shows the effect of substrate loading under the reaction conditions: Solvent, Isopropyl alcohol (95 ml); Temperature 493 K; Pressure, 500 psi; Agitation Speed, 1000 rpm; Catalyst, (3% Pd/C), 0.5 gm; Reaction time 5 h.

Figure 6:
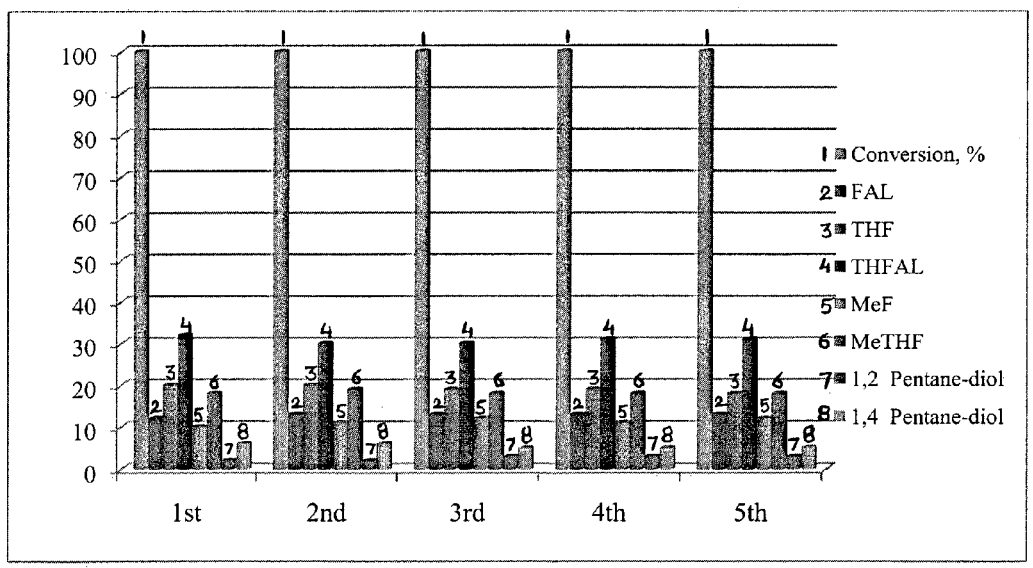

FIG. 6 depicts the catalyst recycle study under the reaction conditions: Furfural, 5% (W/W); Solvent, Isopropyl alcohol (95 nil); Temperature 493 K; Pressure, 500 psi; Agitation Speed, 1000 rpm; Catalyst, (3% Pd/C), 0.5 gm; Reaction time 5 h.

Figure 7:
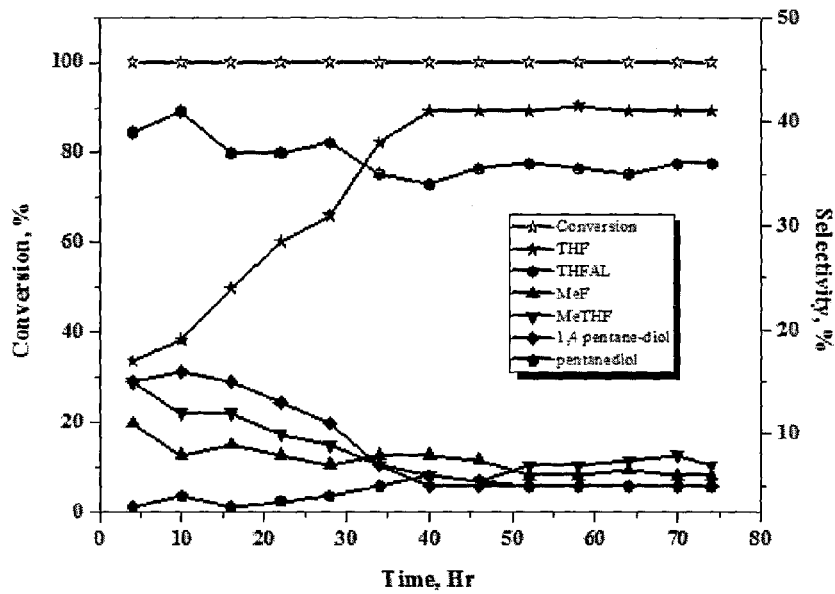

FIG. 7 shows the continuous reaction results conducted under the reaction conditions: Temperature 493 K; Pressure, 500 psi; Feed Flow, 30 mL/hr.

Figure 8:
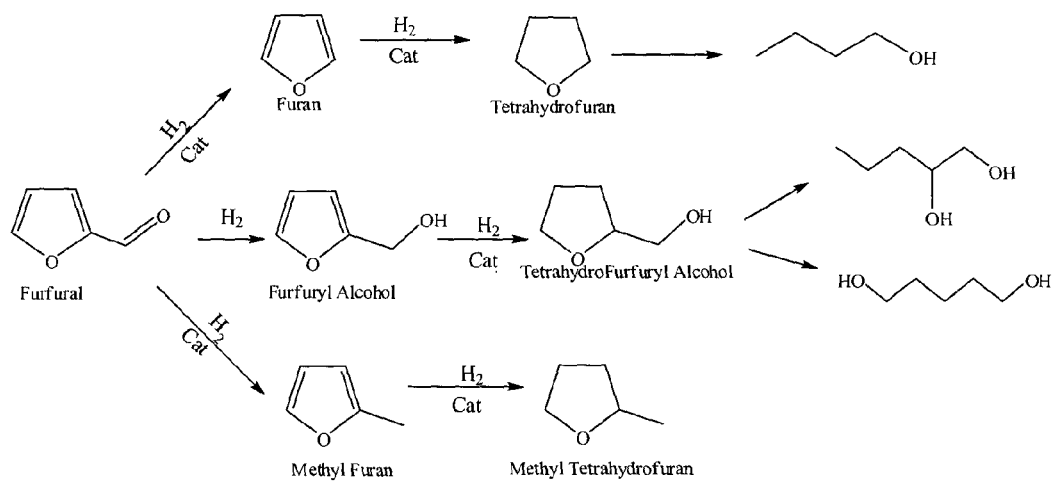

FIG. 8 represents the scheme for general reaction path for furfural hydrogenation.

DETAILED DESCRIPTION OF THE INVENTION

The present invention provides a single step process for production of tetrahydrofuran from hydrogenation of furfural using an effective catalytic system comprising 3% Pd/C, with higher conversion rates and good selectivity. Various parameters such as effects of pressure, temperature, catalyst loading, metals loading, substrate loading on FFR conversion and THF selectivity was studied in batch and continuous operations.

The present inventors have screened variety of catalyst systems selected from noble and non-noble metals on carbon as well as other supports for the conversion of FFR into THF.

Accordingly, the invention discloses an effective catalytic system comprising 3% Pd/C for the conversion of FFR into THF with good selectivity and higher conversion rates in a single step.

A general, reaction path for furfural hydrogenation is given in FIG. 8.

Different supported metal catalysts were screened for the hydrogenation of furfural and their activity; the results of which are shown in Table 1.

TABLE 1

| Catalyst | Conversion % | Selectivity % | | | | | | |
|---|---|---|---|---|---|---|---|---|
| | | FAL | THF | THFAL | MF | MTHF | Pentanediol | Furan |
| % Pd/CaCO$_3$ | 91.5 | 21 | 0 | 69 | 5 | 6 | — | — |
| % Pd/SiO$_2$ | 75.5 | 52 | 3 | 37 | <1 | <1 | 6 | — |
| 3% Pd/C | 100 | 12 | 20 | 32 | 10 | 18 | 8 | — |
| 3% Pt/C | 89.3 | 66 | 0 | 23 | 10 | 1 | — | — |
| 5% Ru/C | 57.3 | 31 | 0 | 40 | 17 | 12 | — | — |
| 3% Re/C | 71.78 | 23 | 0 | 23 | 45 | 10 | — | — |

TABLE 1-continued

| Catalyst | Conversion % | FAL | THF | THFAL | MF | MTHF | Pentanediol | Furan |
|---|---|---|---|---|---|---|---|---|
| CF1 | 100 | >99.5 | 0 | <0.5 | 0 | 0 | — | — |
| NMT005 | 94.1 | 100 | 0 | 0 | 0 | 0 | — | — |
| 10% Ni/C | 100 | 0 | 0 | 5 | 75 | 5 | 15 | — |
| % Pd/CF1 | 100 | 5 | 5 | 11 | 76 | 3 | — | — |
| % Pt/CF1 | 100 | 0 | 0 | 2 | 77 | 2 | — | 18.6 |
| 5% Pd-3% Ru/C | 100 | 2 | 11 | 25 | 3 | 43 | — | 16.84 |

As seen from the above results, 3% Pd/C shows highest selectivity to THF. Using the same catalyst, hydrogenation of furfural was carried out on batch as well as continuous process over various variable parameters is studied.

The invention provides the effect of hydrogen at an elevated pressure on the process.

Accordingly, it was observed that the selectivity of THF is increased from 13% to 20% as the pressure increases from 300 psi to 500 psi. Further the increase in H2 pressure from 500 psi to 750 psi, the selectivity of THF decreases to 18% with the increase in selectivity of other ring hydrogenated products (THFAL and MTHF).

The invention provides effect of temperature on the process, wherein, the selectivity of THF was increased from 15% to 20% as the temperature increased from 473K to 493 K. On further increase in temperature from 493 K to 503 K, a slight decrease in THF selectivity from 20% to 19% was observed with the increase in the other ring hydrogenated products from 50% to 53%.

The invention provides the effect of catalyst concentration on the process, wherein, it was found that as the catalyst loading increased from 0.25 gm to 0.75 gm the selectivity of THF was increased from 14% to 22% confirming that the increase in THF selectivity was mainly due to the increase in number of available catalytic active sites with increasing the catalyst concentration, however, the FFR conversion remains constant.

The invention provides the effect of metal loading on the process of the invention. Accordingly, it was observed that with all the metal loadings, the conversion of FFR remains constant in 5 hrs, while the selectivity of THF increases from 10% to 20% as the metal loading increased from 1% to 3%; at a higher metal loading of 5%, the selectivity of THF decreases to 14%.

The invention provides effect of substrate concentration, wherein, it was observed that a decrease in furfural conversion from 100% to 70% as the concentration of furfural increased from 5 to 20 wt %. The availability of limiting number of available catalytic active sites is responsible for decrease in furfural conversion at high furfural concentration because catalyst amount was constant. The decrease in THF selectivity up to 2% at higher concentration (20%) of furfural was also associated with increase in furan selectivity (35%) which was not observed at 5% wt of FFR. The lower amount of catalyst restricts furan ring for further hydrogenation to THF.

The invention provides catalyst recycle study. According to this study, the reusability of 3% Pd/C catalyst was carried. After the first hydrogenation experiment, the reaction crude was allowed to settle down and the supernatant clear product mixture was separated out. To the catalyst, remaining in the reactor, fresh charge was added and the subsequent hydrogenation was continued. This procedure was followed for four subsequent runs and the results are shown in FIG. 6.

Carbon supported palladium catalyst showed almost the same activity as that of the fresh catalyst even after 4th cycle/reuse.

The process for production of tetrahydrofuran according to the invention may be carried in batch mode or continuous mode. The batch mode may be operated under typical hydrogenation conditions that encompass a temperature of 493 K; hydrogen at a ressure of 3-4 MPa; furfural concentration of 5 wt %; solvent 95 mL and catalyst loading of 0.5 g. Suitable conditions for effective continuous operation include a temperature range of 423-513 K and 20-50 bar pressure. However, effective results are achieved at 30-35H2 bar pressure, with a temperature ranging from 200 to 220 deg C.

Accordingly, the one step process for the synthesis of THF from furfural using 3% Palladium metal based carbon supported catalyst with >10% selectivity and 100% conversion in both batch and continuous modes comprises reacting furfural in the presence of catalyst in the concentration not exceeding 20% at 423-513 K in presence of hydrogen under elevated pressure to obtain THF and related ring hydrogenated products.

EXAMPLES

The following examples are given by way of illustration and therefore should not to be construed to limit the scope of the invention.

Materials

Furfural (99%) was purchased from Sigma-Aldrich, Bangalore, India. Iso-propyl alcohol was purchased from Thomas baker. $PdCl_2$ was purchased from lab-India and activated charcoal was purchased from Sigma-Aldrich, Bangalore, India. Hydrogen of high purity ([99.99%) was obtained from Inox-India Example 1

Catalyst Preparation

Supported Pd/C catalyst was prepared by wet-impregnation method. For the preparation of 3% Pd/C catalyst, 0.159 g of $PdCl_2$ was dissolved in a minimum amount of dilute hydrochloric acid ensuring the complete dissolution of the precursor. Agitation was done with a magnetic stirring bar. Under stirring, 2 g slurry of carbon support prepared in water was added to the above solution, and the temperature was maintained at 353 K. After 1 h, 10 molar sodium hydroxide solution was added under stirring to make pH 7.5 and stirred for half an hour. After half an hour 3 mL of formaldehyde was added under stirring, as a reducing agent. The reaction mixture further stirred for half hour and was then cooled and filtered to obtain the catalyst, which was dried at 100° C.

The catalyst thus obtained was characterized for BET surface area on Chemisorb 2720 Micromeritics instrument by nitrogen adsorption at 77K.

Example 2

Catalyst Activity

The performance of the prepared catalyst was tested on both, batch as well as continuous process.

i. Batch Operation

Batch reactions were carried out in 300 mL capacity autoclave at an agitation speed of 1000 rpm supplied by Parr Instruments Co. USA. The typical hydrogenation conditions were: temperature, 493 K; hydrogen at a pressure in the range of 3-4 MPa; furfural concentration, 5 wt %; solvent 95 mL and catalyst loading, 0.5 g.

ii. Continuous Operation

Continuous hydrogenation of furfural was carried out in a bench scale, high-pressure, fixed-bed reactor supplied by M/s Geomechanique, France. This reactor set up consisted of a stainless steel single tube of 0.34 m length and 1.5×10-2 m inner diameter. The reactor was heated by two tubular furnaces whose zones (TIC1 and TIC2) were independently controlled at the desired bed temperature. The reactor was provided with mass flow controllers, pressure indicator, and controller (PIC) devices and two thermocouples to measure the temperature at two different points. A storage tank was connected to the HPLC pump through a volumetric burette to measure the liquid flow rate. The pump had a maximum capacity of 3×10-4 m3/h under a pressure of 100 bar. The gas-liquid separator was connected to other end of the reactor through a condenser.

Ten gm of the powder catalyst was charged in to the reactor. The section of $7 \times 10^{-2}$ m above and $7 \times 10^{-2}$ m below the catalyst bed was packed with carborandum as an inert packing, and remaining reactor was filled with catalyst powder in four sections, where the sections are separated by carborandoms. Before starting the actual experiment the reactor was flushed thoroughly, first with $N_2$ and then with $H_2$ at room temperature. Then the reactor was pressurized with $H_2$ after attaining the desired temperature. The liquid feed was "switched on" after the reactor reached the operating pressure and was kept at that value for 1 h to obtain the constant liquid flow rate. Liquid samples were withdrawn from time to time. Samples taken during the reaction were analyzed with a Trace GC 700 series GC System (Thermo SCINTIFIC) coupled with FID detector and capillary column (HP-5 capillary column, 30 m length×0.32 mm id). The following temperature programme method was used for GC analysis: 40° C. (3 min)-1° C./min-45° C. (1 min)-10° C./min-60(0 min)-20° C./min-250 (1 min).

Following this procedure, the experiments were carried out at different inlet conditions of liquid and gas flow rates. The reactor was operated in the temperature and pressure ranges of 423-513 K and 20-50 bar, respectively. Steady-state performance of the reactor was observed by analysis of the reactant and products in the exit stream.

The conversion and selectivity were calculated and defined as follows:

$$(\%) \text{Conversion} = \frac{\text{Initial moles.of Furfural} - \text{Final moles.of Furfural}}{\text{Initial moles.of Furfural}} \times 100 \quad (1)$$

$$(\%) \text{Selectivity} = \frac{\text{Moles of a product formed}}{\text{Moles of Furfural consumed}} \times 100 \quad (2)$$

Example 3

Catalyst Activity Testing in Batch Operation a) Effect of Hydrogen at an Elevated Pressure FIG. 1 shows the effect of hydrogen at an elevated pressure on FFR hydrogenation at 493 K. The selectivity of THF is increased from 13% to 20% (other ring hydrogenated products MTHF and THFAL 50%) as the pressure increased from 300 psi to 500 psi. Further increase in $H_2$ pressure from 500 psi to 750 psi, the selectivity of THF decrease to 18% and selectivity of other ring hydrogenated products (THFAL and MTHF) increased from 50% and 58%. The increase in other ring hydrogenated product is due to strong interaction between the metal and the ☐ bonds in the furan molecule.

b) Effect of Temperature

FIG. 2 shows effect of reaction temperature on conversion and selectivity at 500 psi $H_2$ pressure. The selectivity of THF was increased from 15% to 20% as the temperature increased from 473K to 493 K. On further increase in temperature from 493 K to 503 K there is slight decreased in THF selectivity from 20% to 19% was observed. This is again leads in increasing the other ring hydrogenated products from 50% to 53%.

c) Effect of Catalyst Concentration

The effect of catalyst concentration on the conversion of furfural and selectivity of THF was also studied in the range of 0.250-0.750 g at 493 K and 500 psi $H_2$ pressure and the results are shown in FIG. 3. It was found that as the catalyst loading increased from 0.25 gm to 0.75 gm the selectivity of THF was increased from 14% to 22%. The increase in THF selectivity was mainly due to the increase in number of catalytic active sites with increasing the catalyst concentration. FFR conversion was remaining constant.

d) Effect of Metal Loading

The effect of Pd metal loading on carbon in the range of 1% to 5% on selectivity of THF was also studied and the results are shown in FIG. 4. For all the metal loading conversion of FFR remains constant in 5 hrs, while the selectivity of THF increased from 10% to 20% as the metal loading increased from 1% to 3%. At a higher metal loading of 5%, the selectivity of THF decreases to 14%.

e) Effect of Substrate Concentration

The effect of furfural concentration on hydrogenation reactions was studied in the range of 5-20 wt % furfural and the results are shown in FIG. 5. The decreased in furfural conversion was observed from 100% to 70% as the concentration of furfural increased from 5 to 20 wt %. The availability of limiting number of catalytic active sites is responsible for decrease in furfural conversion at high furfural concentration because catalyst amount was constant. The decrease in THF selectivity up to 2% at higher concentration (20%) of furfural was also associated with increase in furan selectivity (35%) which was not observed at 5% wt of FFR. The lower catalyst restricted furan ring for further hydrogenation to THF.

f) Catalyst Recycle Study

The catalyst reusability studies for 3% Pd/C catalyst was carried out as follows. After the first hydrogenation experiment, the reaction crude was allowed to settle down and the supernatant clear product mixture was separated out. To the catalyst, remaining in the reactor, fresh charge was added and the subsequent hydrogenation was continued. This procedure was followed for four subsequent runs and the results are shown in FIG. 6. Carbon supported palladium catalyst showed almost the same activity as that of the fresh catalyst even after 4th reuse.

g) Screening of Substrates

In order to understand the reaction mechanism, the different FFR hydrogenation products were taken as substrate and tested on same reaction parameters the results are shown in Table 2. It was observed that on hydrogenation only corresponding ring hydrogenated products were formed. So from the results it was confirmed that the hydrogenation of the FFR to THF carried out via furan i.e. first hydrogenation of FFR to furan and then to THF.

Example 4

Continuous Operation

As mentioned above, 3% Pd/C catalyst gives highest selectivity to THF in the batch operation; hence the same catalyst is taken for the continuous process.

The continuous hydrogenation reaction was carried out at 493 K temperature and 500 psi $H_2$ pressure. The conversion of FFR was remains 100% as in the continuous process and the THF selectivity was increased from 20% to 41% as compared to batch process and the other ring hydrogenated product were 42% (THFAL 36%, MTHF 7%), the results are shown in FIG. 7. Initially the selectivity was 20% at 10 hrs, after 40 hrs the selectivity of THF was 41% and it remains constant up to 74 hrs. The increase in selectivity of THF (41%) is due to lower the contact time of substrate to catalyst as compare to batch process.

TABLE 2

| Compound | Conversion % | Selectivity, % | | | | | | |
|---|---|---|---|---|---|---|---|---|
| | | FA | THF | THFAL | MF | MTHF | Pentanediol | Furan |
| 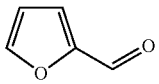<br>Furfural | 100 | 12 | 20 | 32 | 10 | 18 | 8 | — |
| 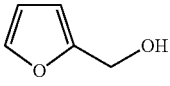<br>Furfuryl alcohol<br>FA | 100 | SM | — | 100 | — | — | — | — |
| 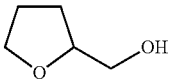<br>TetrahydroFurfuryl alcohol<br>THFA | — | — | — | SM | — | — | — | — |
| 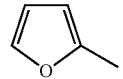<br>Methyl Furan<br>MF | 100 | — | — | — | SM | 100 | — | — |
| <br>Furan | 100 | — | 100 | — | — | — | — | SM |

Reaction Conditions: Substrate, 5% (W/W); Solvent, Isopropyl alcohol (95 ml); Temperature, 493 K; Pressure 500 psi; Agitation Speed, 1000 rpm; Catalyst, (3% PdMFI), 0.5 gm; Catalyst, 0.5 gm; Reaction time 5 h.
SM: Starting Molecule.
MTHF: METHYL TETRAHYDROFURAN
FFR: FURFURAL Comparative Example

| Parameters | Present Invention | D1 | D2 | D3 | U.S. Pat. No. 7,425,657 B1 | U.S. Pat. No. 7,956,203 | US 2010/0048922 | D7 |
|---|---|---|---|---|---|---|---|---|
| Type of Reaction | Single Step hydrogenation | Electrolytic reduction | Hydrodeoxygenation | Hydrogenation | Hydrogenation | Decarbonylation | Catalytic hydrogenation | Hydrogenation |
| Batch or continuous | Both | Continuous | — | Batch | Batch | Batch | Batch | Continuous |
| No. of steps in process | One step | One step | — | One step | One step | One step | One step | Two step |
| Catalyst | 3% Pd/C | 1% Pd/C | — | 5% Ru/C | Pd and Ru | | Noble and non noble | 5% Pd/SiO2 |
| Temperature | 220° C. | 30-70° C. | — | 350° C. | 200-300° C. | | — | 230° C. |
| Final Product | THF, THFAL, MeF, MeTHF, 1,2 & 1,5-Pentanediol | FA, THFA, MF, and MTHF | — | oil | bio-oil | furan | 2-MeF | Furan, THF |
| Selectivity, % | 41*, 36, 6, 7, 5, 5 | 54, 28, 8, 8 | — | 65 | — | — | — | 60, 20 |

*41% in a continuous reactor.
20% in batch reactor.
D1: The electrocatalytic hydrogenation of furanic compounds in a continuous electrocatalytic membrane reactor by Sara K. Green, Jechan Lee, Hyung Ju Kim, Geoffrey A. Tompsett, Won Bae Kim and George W. Huber in *Green Chem.*, 2013,15, 1869-1879.
D2. Furfural Deoxygenation Over Carbon-Supported Noble Metal Catalysts by Simon T. Thompson and H. Henry Lamb
D3. Insights in the hydrotreatment of fast pyrolysis oil using a ruthenium on carbon catalyst by Jelle Wildschut, Muhammad Iqbal, Farchad H. Mahfud, Ignacio Meli_an Cabrera, Robbie H. Venderbosch and Hero J. Heeres in Energy Environ. Sci., 2010, 3, 962-970.
D7. Hydrodeoxygenation of Furfural Over Supported Metal Catalysts: A Comparative Study of Cu, Pd and Ni by Surapas Sitthisa, Daniel E. Resasco in Catal Lett (2011) 141: 784-791.

Advantages of the Invention

1. Efficient catalyst system
2. Good selectivity
3. High conversion rate

We claim:

1. A one step process for the synthesis of Tetrahydrofuran (THF) from furfural in both batch and continuous modes comprising: reacting furfural at a concentration in the range of 5 to 20% in the presence of Palladium metal based carbon supported catalyst at a concentration in the range of 5 to 20% at a temperature in the range of 423-513 K in presence of hydrogen at an elevated pressure to obtain THF with 10% to 41% selectivity and related ring hydrogenated products, wherein conversion percentage of furfural is 100%.

2. The process according to claim 1, wherein the concentration of furfural is 5% by weight.

3. The process according to claim 1, wherein the selectivity is 20% for batch mode and 41% for continuous mode.

4. The process according to claim 1, wherein the elevated pressure is in the range of 3 to 4 MPa for batch mode and 20 to 50 bar pressure for continuous mode.

5. The process according to claim 4, wherein the elevated pressure is in the range of 30-35 bar pressure for continuous mode.

6. The process according to claim 1, wherein the yield of THF is in the range of 20% for batch mode and 40% for continuous mode.

7. The process according to claim 1, wherein the temperature is 493 K for batch mode and in the range of 423 to 513 K for continuous mode.

8. The process according to claim 7, wherein the temperature is in the range of 473 to 493 K for continuous mode.

9. The process according to claim 1, wherein the related ring hydrogenated products are selected from the group consisting of methyl tetrahydrofuran (MTHF), tetrahydrofurfuryl alcohol (THFAL), Methyl Furan, and Pentanediol.

10. The process according to claim 1, wherein said catalyst is recyclable.

* * * * *